:::
United States Patent [19]

Humphrey

[11] Patent Number: 5,176,028

[45] Date of Patent: Jan. 5, 1993

[54] DEVICE FOR TESTING ADHESIVE BONDS

[75] Inventor: Philip E. Humphrey, Corvallis, Oreg.

[73] Assignee: The State of Oregon acting by and through the Oregon State Board of Higher Education on behalf of Oregon State University, Eugene, Oreg.

[21] Appl. No.: 591,119

[22] Filed: Oct. 1, 1990

[51] Int. Cl.$^5$ ............................................. G01N 3/24
[52] U.S. Cl. .................................. 73/150 A; 73/842; 374/45
[58] Field of Search ...................... 73/150 A, 842, 827, 73/842; 374/45

[56] References Cited

U.S. PATENT DOCUMENTS

| 2,982,129 | 5/1961 | Wetzel et al. | |
|---|---|---|---|
| 2,989,865 | 6/1961 | Belfour | 73/150 A |
| 3,412,606 | 11/1968 | Cooper et al. | 73/150 A |
| 3,850,033 | 11/1974 | Schmitt | |
| 4,253,901 | 3/1981 | Aslakson | 73/150 A X |
| 4,856,342 | 8/1989 | Bottenbruch et al. | |
| 4,893,513 | 1/1990 | Schroeder et al. | 73/150 A X |
| 4,957,004 | 9/1990 | McKinlay et al. | 73/842 |

FOREIGN PATENT DOCUMENTS

| 54-1088 | 1/1979 | Japan | 73/150 A |
|---|---|---|---|
| 0276483 | 5/1969 | U.S.S.R. | 73/842 |
| 0800835 | 2/1981 | U.S.S.R. | 73/842 |

OTHER PUBLICATIONS

"A Technique to Evaluate the Bonding Reactivity of Thermosetting Adhesives," P. E. Humphrey, D. Zavala, pp. 323-328, Nov. 7, 1989.

Primary Examiner—Daniel M. Yasich
Attorney, Agent, or Firm—Klarquist, Sparkman, Campbell, Leigh & Whinston

[57] ABSTRACT

An adhesive is applied to overlapping portions of a two-part test sample located between opposing press heads of the bond testing device. The press heads then press together the overlapping portions for a specific period of time while heating the test sample to a preselected temperature. The device precisely maintains the temperature while bonding the sample at a preselected pressure. A load cell measures the shear force required to separate the bonded test piece.

17 Claims, 5 Drawing Sheets

DEVICE FOR TESTING ADHESIVE BONDS

BACKGROUND OF THE INVENTION

This invention relates to devices for testing the strength development of adhesive bonds.

Devices for testing the strength of adhesive bonds currently exist. For instance, Wetzel et al., U.S. Pat. No. 2,982,129, describe a method for testing the bonding strength of gummed tape by determining the force necessary to shear the adhesive bond developed between the gummed tape and a backing.

In many applications, it is useful to know how the development of adhesive bonding strength between two parts is affected by temperature, curing time, or the pressure that is applied to adhere the two parts. For example, a process for manufacturing laminated material, such as plywood, can be made most efficient when the precise relationship among process variables (temperature, curing time, and pressure) is known so that the process can be adjusted to develop in the material the minimum required bonding strength between layers in the shortest time period.

Determining the relationship among process variables and adhesive bonding strength could be effectively and efficiently accomplished by a compact testing device that is readily adjustable for duplicating any of a plurality of process variables that affect the development of adhesive bonding strength, and that reliably provides data indicative of the adhesive bonding strength for any selected combination of those process variables.

SUMMARY OF THE INVENTION

This invention is directed to a compact device for forming and immediately thereafter testing adhesive bonds. The device includes interconnected mechanisms for pressing together test sample parts to form the adhesive bond between those parts, and for forcing apart the bonded parts while measuring the maximum force required to overcome the adhesive bond.

The two-part test sample is constructed of two parts that overlap at the center of the sample. Adhesive is applied to the overlapping portion of the test sample before the parts are brought together.

Opposing press heads press together the overlapping portion of the test sample to facilitate formation of the bond.

The device includes clamps for clamping the opposite ends of the two-part test sample and for forcing apart the clamped ends of the test sample to cause failure of the adhesive bond. The force required to cause the failure (that force representing the adhesive bond strength) is detected and recorded.

The versatility of the device is enhanced with mechanisms for duplicating any of a number of process variables that may affect the way an adhesive bond develops strength. Specifically, mechanisms are provided for heating to a preselected temperature the bonded, overlapping portion of the test sample while the overlapping portion is pressed together. The temperature can be changed from sample to sample, or during formation of one sample, so that data representing the relationship between bonding strength development and temperatures can be compiled.

The data pertaining to the relationship between bond strength development and temperature is usually most useful when converted into a series of isothermal strength development curves. The device of the present invention is capable of rapidly heating a test sample to a constant temperature and precisely maintaining that temperature as the sample is pressed and bond strength is measured. Repetition of this procedure for different temperatures creates the series of isothermal strength development curves for enabling study of the effects of temperature on bond strength development.

The pressure applied by the press heads and the time interval during which the overlapping portion is pressed together may be established at any of a multitude of values selected by the user of the device. Data representing the relationship between bonding pressure and bond strength are, therefore, readily compiled.

The device is particularly useful and precise when testing lap-bonded parts. In this regard, the device is operable so that only shear force is applied in testing the sample. The test sample is controlled so that is does not twist or bend during the test.

Operation of the device is carried out with a pneumatic control system that is automated for efficiently testing a multitude of samples.

DETAILED DESCRIPTION

Figure 1:
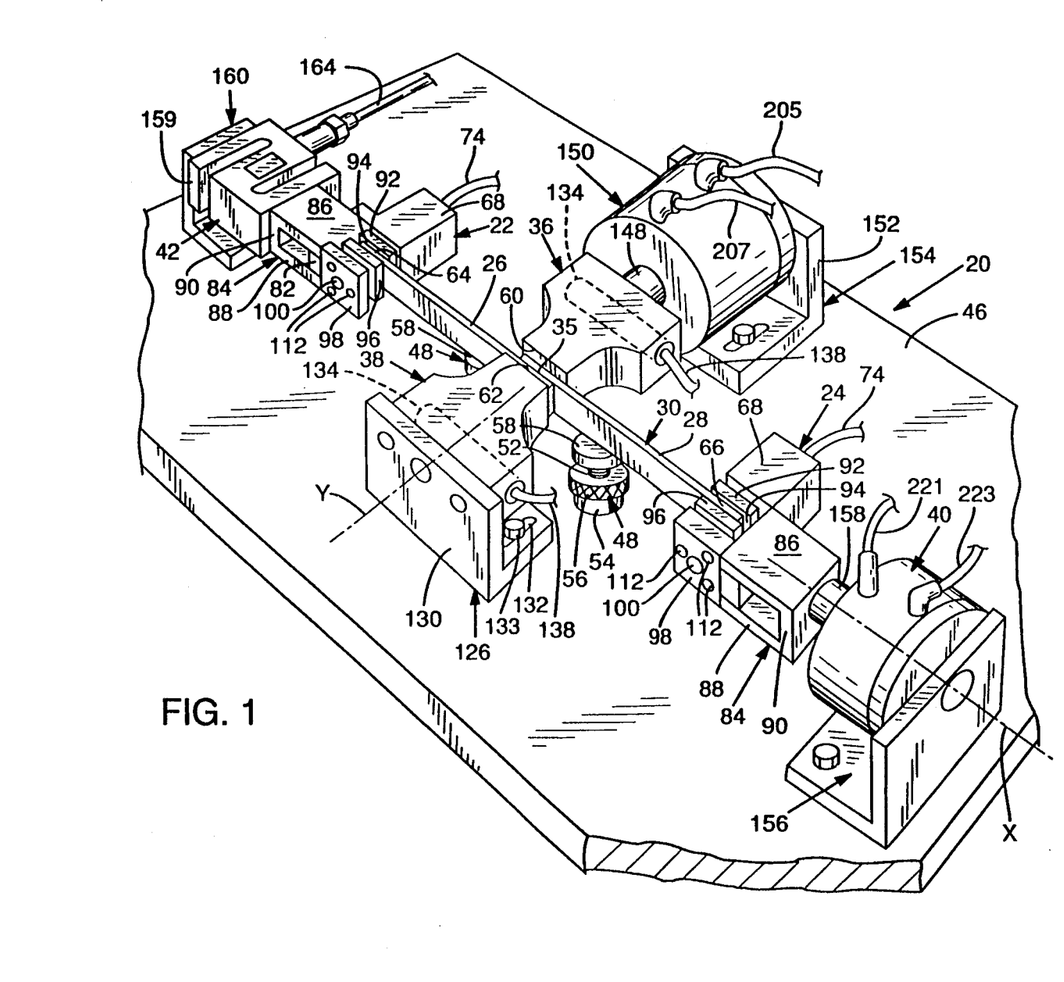
FIG. 1 is a diagrammatic top perspective view of the device of the present invention.
Figure 2:
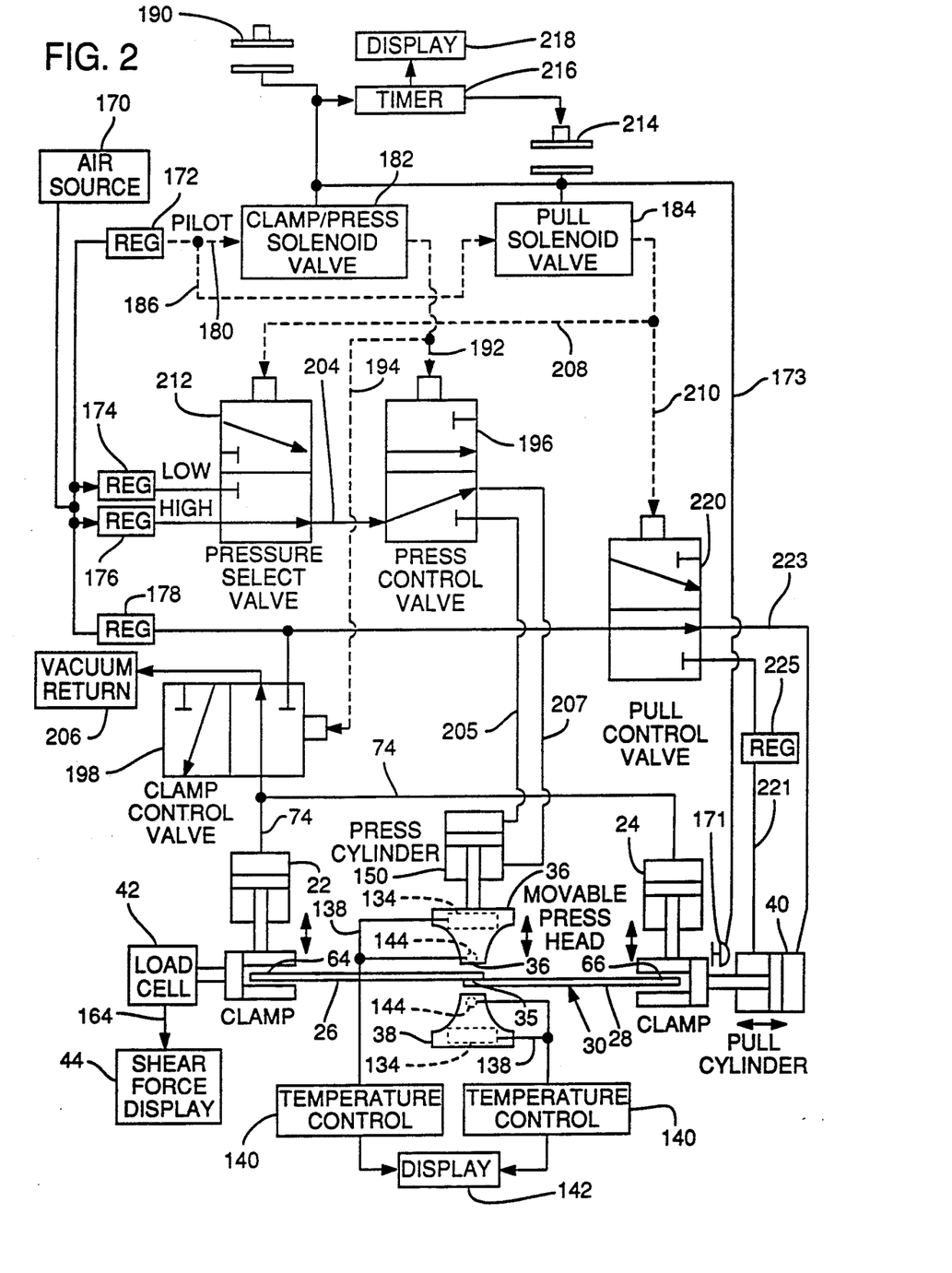
FIG. 2 is a schematic/block diagram of the device, including the control system.
Figure 3:
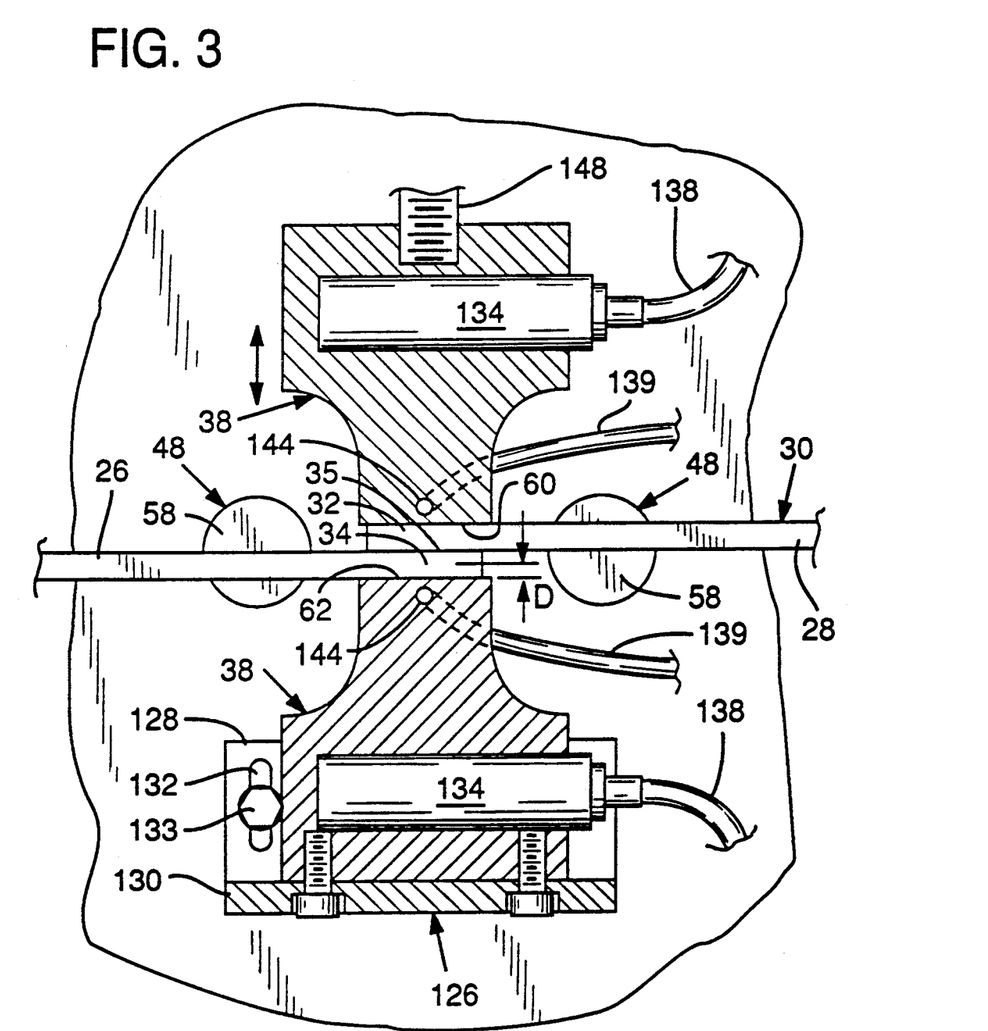
FIG. 3 is a top plan cross-sectional view showing the press heads pressing together two parts of a test sample.

Referring to FIGS. 1-3, the device 20 of the present invention includes two clamp mechanisms 22, 24 for clamping two parts 26, 28 of a test sample 30. The test sample 30 is formed by applying an adhesive between overlapping portions 32, 34 of the sample parts 26, 28. Hereafter, the overlapping portions 32, 34 of the test sample 30 will occasionally be referred to as the bonding region 35 of the test sample. It is contemplated that the test parts may inherently have, or be treated to have, adhesive properties that would obviate the need for applying additional adhesive to the bonding region 35.

The bonding region 35 is pressed between two heated press heads 36, 38. After the bonding region 35 has been pressed between the heads 36, 38 for a preselected time, the pressure applied to the bonding region 35 is reduced and one clamp mechanism 24 is pulled away from the other clamp mechanism 22 by a pneumatically operated "pull" cylinder 40. The other clamp mechanism 22 is connected to a load cell 42 that provides output signals indicative of the force applied to the test sample 30, including the maximum force applied before failure of the bond between the overlapping portions 32, 34.

The output signals from the load cell 42 are converted to the corresponding shear force developed in the bonding region 35 of the test sample 30. That force is indicated on an associated display device 44, and may be considered as the peak shear load sustained by the bond.

Turning to the particulars of the present invention, and with reference to FIGS. 1-5, many of the components of the device 20 are mounted to a desk-top sized platform 46. A pair of spaced-apart sample supports 48 (FIGS. 1 and 5) are mounted near the center of the platform 46. Each sample support 48 includes a cylindrical head 50 having an attached threaded shaft 52. The shaft 52 is threaded into a nut 54 that is fastened to the platform 46 around a clearance hole in the platform. A knurled lock nut 56 is also threaded over the shaft 52 of the sample support 48 between the nut 54 and the cylindrical head 50.

The flat upper surface 58 of the support head 50 provides support for the test sample 30 at the correct elevation above the platform 46 so that the bonding region 35 of the test sample will be aligned between the planar press faces 60, 62 of the press heads 36, 38, as described more fully below.

The elevation of the upper surface 58 of each sample support 48 is adjusted by threading the shaft 52 into or out of the nut 54. Once the correct elevation is established, the knurled lock nut 56 is tightened against the platform nut 54 to secure the support 48 at the correct elevation.

The test sample 30 can be any of a number of materials and configurations. In one embodiment, the sample 30 comprises two 0.8 millimeter (mm) thick strips of wood, each strip being 100.00 mm long and 15.0 mm wide. The amount of overlap between the two wood parts 26, 28 is 15.0 mm. Accordingly, the area of the bonding region 35 is 225.0 mm$^2$. It is preferred that the sample be made as thin as practical so that the heat applied to the sample by the press heads 36, 38 is rapidly transferred to the bonding region 35.

As shown in FIG. 1, a line through the centers of the sample supports 48 defines one reference axis "X", and the line perpendicular to the X axis and between those supports defines a "Y" reference axis.

The test sample 30 is placed upon the sample supports 48 so that the bonding region 35 is centered about the Y axis, and so that the surfaces of the overlapping portions 32, 34 of the test sample 30 are in a plane that is parallel to the planar press faces 60, 62 of the press heads 36, 38.

Each free end 64, 66 of the test sample parts 26, 28 is held in a clamp mechanism 22, 24. Only one clamp mechanism 22 is now described because the other clamp mechanism 24 is substantially identical. Accordingly, identical parts in both clamp mechanisms 22, 24 will carry identical reference numerals.

Figure 4:
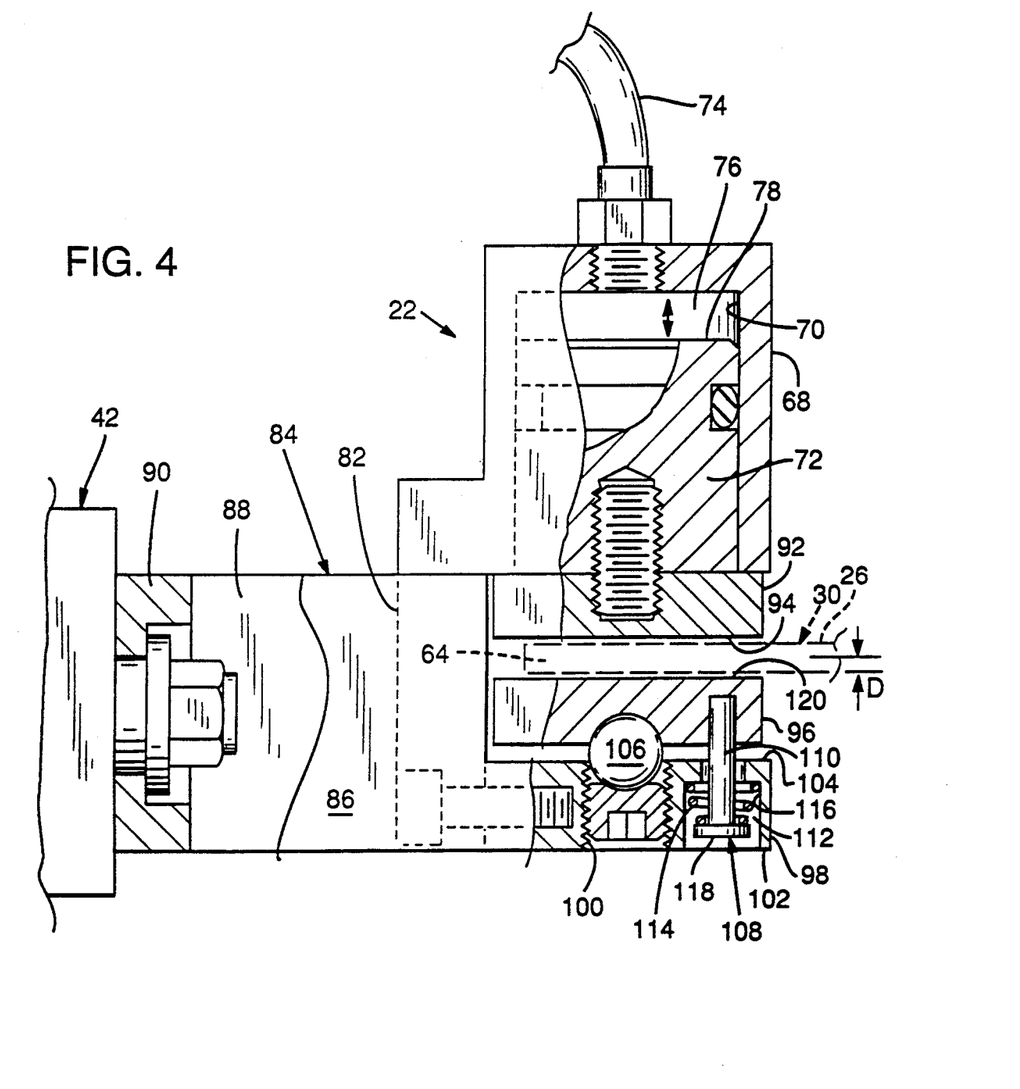
FIG. 4 is a top plan detail view, in partial section, showing a clamp mechanism used with the device of the present invention.
Figure 5:
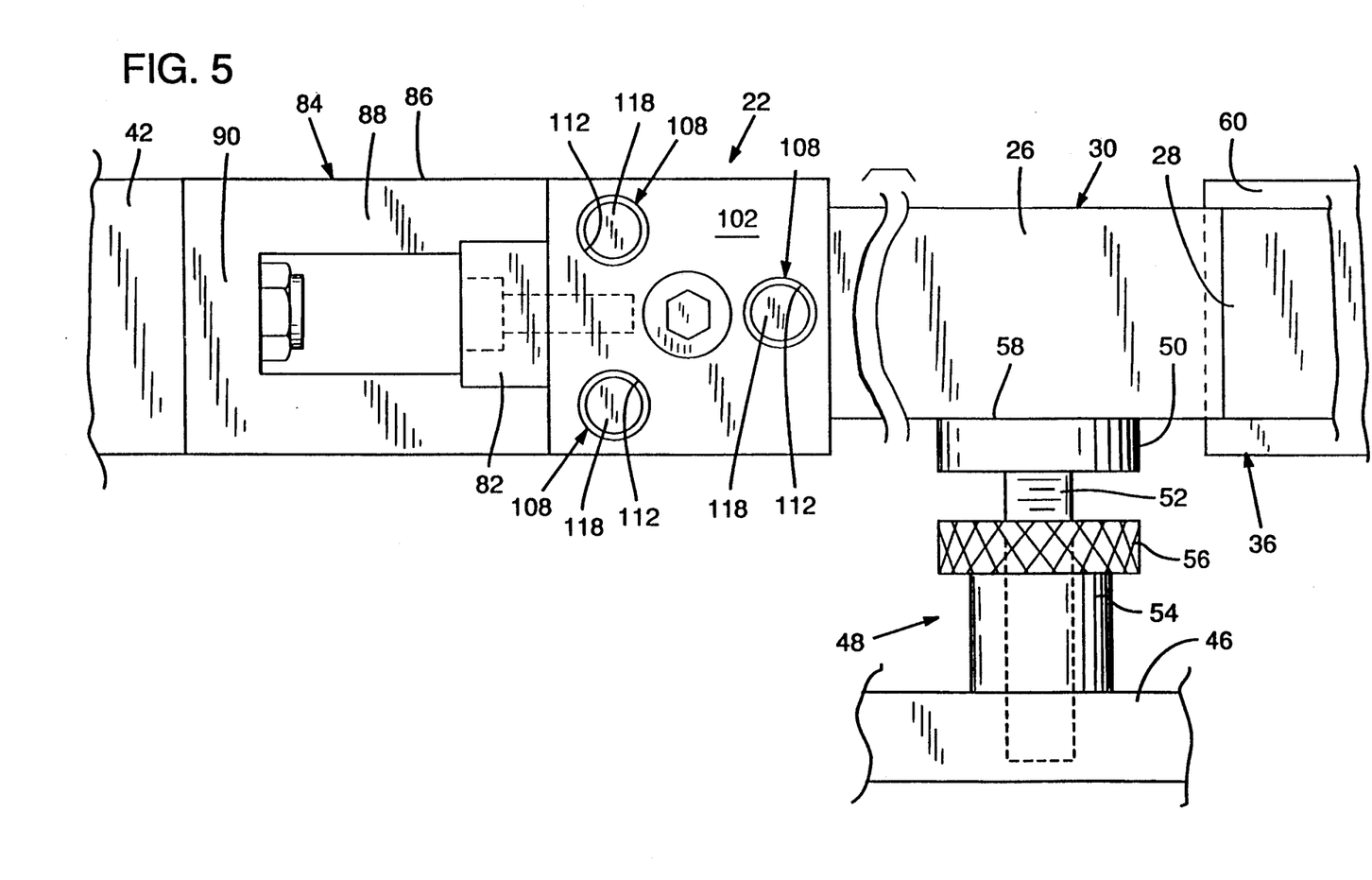
FIG. 5 is a side elevation detail view of a clamp mechanism.

As best shown in FIGS. 4 and 5, the clamp mechanism 22 includes a rigid cylinder block 68 that has a central cylindrical bore 70. A cylindrical piston 72 slides within the bore 70 under the influence of pneumatic pressure or vacuum applied, via pneumatic line 74, to the enclosed chamber 76 that is defined by the walls of bore 70 and the rear face 78 of the piston 72.

One side of the cylinder block 68 includes a flat bracket 82 that protrudes outwardly from the block 68. The protruding bracket 82 is mounted to a generally C-shaped mounting bracket 84. The mounting bracket 84 includes a top plate 86, bottom plate 88, and a back plate 90. The back plate 90 is fastened to extend between the ends of the top plate 86 and bottom plate 88. The protruding bracket 82 fits between and is fastened to the other ends of the mounting bracket 84.

A flat clamp plate 92 is fastened to the front face of the piston 72. The clamp plate 92 has a planar clamp face 94 that bears against the free end 64 of the test sample part 26. The clamp plate 92 travels with the piston 72, parallel to the Y axis, toward and away from a floating clamp plate 96 for respectively clamping and releasing the test sample end 64.

The floating clamp plate 96 is mounted to a rigid backing plate 98 that is fastened to the mounting bracket 84 and protrudes outwardly therefrom. The backing plate 98 includes a central threaded aperture 100 that extends from the outer face 102 to the inner face 104 of the plate 98. A ball bearing 106 having a diameter slightly greater than the diameter of the central aperture 100 is seated between the opening of the aperture 100 in the inner face 104 and a correspondingly shaped recess in the floating clamp plate 96.

Three headed guide screws 108 are threaded into the floating clamp plate 96 at uniformly spaced locations about the center of the floating clamp plate 96. The shaft 110 of each guide screw 108 fits through a counterbored hole 112 formed through the backing plate 98. A compression spring 114 is located around each shaft 110 and is held within the counterbored portion 116 of the hole 112 by the head 118 of the guide screw 108. The springs 114 force the screws 108 and attached floating clamp plate 96 toward the backing plate 98 so that the clamp plate 96 remains seated against the ball bearing 106.

The clearance between the guide screws 108 and the hole 112 in the backing plate 98 permit the clamp plate 96 to pivot about the ball bearing 106 so that the planar clamp face 120 of the clamp plate 96 will press uniformly against the surface of the test sample end 64 whenever the piston 72 is activated to clamp the test sample end 64 between the clamp plates 92, 96.

As will become clear upon reading this description, the accuracy and consistency in testing the shear strength of adhesive bonds is enhanced where no bending is introduced into the test sample 30 as it is pulled apart. Accordingly, it is desirable to clamp the test sample 30 so that each test part 26, 28 remains straight during the test. Moreover, the longitudinal axis of the test parts 26, 28 should be parallel to the X axis as the bonding region 35 is pulled apart. To this end, the clamp mechanisms 22, 24 include means for ensuring that the longitudinal axes of the test sample parts remain straight and parallel to the X axis, irrespective of differences in thicknesses from one test sample type to another.

The adjustment means (see FIG. 4) include a set screw 122 that is threaded into the central aperture 100 of the backing plate 98. One end of the set screw 122 is cupped to conform to the shape of the ball bearing 106. As the set screw 122 is threaded into or out of the aperture 100, the floating clamp plate 96 moves toward or away from the backing plate 98. It can be appreciated, therefore, that the location of planar clamp face 120 of the clamping plate 96 may be adjusted to be precisely spaced from the center of the test sample part 26 by a distance D corresponding to one half of the thickness of the sample part 26. As will be described below, the press head 38 is also adjustable to be spaced the distance D from the center of the straight test part 26 (see FIG. 3). As a result, when the test part 26 is pressed between the clamp faces 94, 120, sample part 26 will remain substantially straight.

As mentioned above, the clamp mechanisms 22, 24 are pulled apart after the adhesive bond between the test parts 26, 28 is formed. The press heads 36, 38 for forming the bond are disposed on opposite sides of the test sample bonding region 35 and centered on the Y axis.

One press head 38 remains stationary during the pressing operation. That head 38 is mounted to an L-shaped bracket 126 that has a horizontally extending base 128 and a vertically extending wall 130. The base 128 of the bracket 126 is fastened to the platform 46. Preferably, the base 128 includes elongated openings 132 through which extend the shafts of headed fasteners 133 that are used to fasten the bracket 126 to the platform 46. The openings 132 permit adjustment of the bracket location relative to the X axis so that the planar face 62 of the press head 38 may be located, relative to the X axis, to match the thickness of the test sample part 26. Put another way, the adjustment of the planar face 62 permits the stationary planar face 62 of the press head 38 to be coplanar with the planar face 120 of the floating clamp plate 96 of the clamp mechanism 26 that holds the sample part 22 that is nearest that head 38. As a result, the test sample 30 will not bend as the moving press head 36 is pressed against the bonding region 35 of the sample 30.

The width (that is, as viewed in top plan) of the press head 38 is gradually reduced from about the middle of the press head 38 to the planar face 62 of the head. The press head 38 is fastened to the vertically extending wall 130 of the bracket 126. A resistive type heater 134 is sealed within an opening within the press head 38. The leads 138 from the heater 134 connect with a temperature controller 140 (FIG. 2) that includes a display 142 for displaying the temperature selected by the user. The temperature of the press head 38 is regulated by the temperature controller 140 in response to signals received from a thermocouple 144 that is embedded within the press head 38 very near the press face 62.

The movable press head 36 has the same shape as the stationary press head 38 and includes a heater 134 sealed therewithin. The heater 134 in the movable head 36 is connected to a temperature controller 140 and associated thermocouple 144 embedded in the press head 36 near the planar face 60.

The temperature controllers 140, heaters 134, and thermocouples, 144 may be components of any conventional temperature controller system, such as that available from Omega Engineering, Inc., of Stamford, Conn., as Model No. CN9111.

The back of the movable press head 36 is connected to the exposed nonrotatable rod 148 of a pneumatically operated press cylinder 150. The press cylinder 150 is fastened to the vertically extending wall 152 of an L-shaped bracket 154 that is mounted to the platform 46.

The press cylinder 150 presses the movable press head 36 against the stationary press head 38 with the bonding region 35 of the test sample therebetween. After the press head 36 has been pressed against the bonding region 35 for a preselected time period, the pneumatic pressure in the cylinder 150 is reduced. As a result, the pressure applied by the press head 36 is small so not to siqnificantly resist (e.g., by friction) the shearing force imparted by the pull cylinder 40 as described below. The press head 36 does not retract from the bonding region 35 as long as the reduced pressure is applied.

Once the press cylinder 150 reduces the bonding pressure, the pull cylinder 40 is actuated to pull one clamp mechanism 24 away from the other clamp mechanism 22 to cause failure of the test sample bond. The load cell 42, which is connected to the other clamp mechanism 22, measures the shear force developed up to the instant of the failure of the bond.

The pull cylinder 40 is mounted to an L-shaped bracket 156 that is fastened to the platform 46. The exposed nonrotatable rod end 158 of the pull cylinder 40 is connected to the back plate 90 of the mounting bracket 84 to which one clamp mechanism 24 is mounted.

One end 159 of the load cell 42 is mounted to an L-shaped bracket 160 that is fastened to the platform 46. The other end 162 of the load cell is fastened to the back plate 90 of the mounting bracket 84 to which the other clamp mechanism 22 is mounted.

The platform 46 is provided with a plurality of holes for mounting the L-brackets 156, 160 at any selected distance apart from one another. It can be appreciated, therefore, that the distance between the clamp mechanisms 22, 24 may be established so that sample parts 26, 28 can be clamped thereto to provide any desired amount of overlap within the bonding region 35. To this end, the brackets 156 may also include elongated openings such as those 132 described with respect to brackets 126, 154.

The shear force applied to the test sample 30, which is developed as the pull cylinder 40 retracts the clamp mechanism 24, is transmitted via clamp mechanism 22 and associated mounting bracket 84 to the load cell 42. The load cell 42, which may be a model "LCC", as manufactured by Omega Engineering, Inc., of Stamford, Conn., applies on output line 164 a signal indicative of the force applied to the test sample 30. That signal is converted into appropriate units and indicated on the associated display device 44.

It is noteworthy that as the pull cylinder 40 retracts the clamp mechanism 24, the planar faces 60, 62 of the press heads 36, 38 remain in contact with the bonding region 35 of the test sample 30. The press faces 60, 62 thereby prevent any twisting or bending in the bonding region 35 so that the force applied to the bonding region will comprise only a shearing force.

The mechanisms for controlling the operation of the device 20 are now described with particular reference to FIG. 2. Preferably, the clamp mechanisms 22, 24, press cylinder 150, and pull cylinder 40 are all pneumatically operated, although hydraulic or electrical control means may be readily substituted.

A pressurized air source 170 is branched through four regulators 172, 174, 176, 178 to provide separate sources of regulated pressurized air. One regulator 172 provides a source of pilot air over pilot line 180 to a clamp/press solenoid valve 182, and to a pull solenoid valve 184 over pilot line 186.

The clamp/press solenoid valve 182 is activated by an associated switch 190 after the sample 30 is properly located with the bonding region 35 between the press heads 36, 38, and the free end 64, 66 located between the clamp plates 92, 96 of the clamp mechanisms 22, 24.

It is noteworthy here that the switch 190 that actuates the clamp/press solenoid valve 182 to initiate tha clamping and pressing operation may be controlled by any suitable mechanism for automating the testing process. For example, a proximity detector or limit switch may be located near the press heads 36, 38 and actuated whenever the test sample 30 is properly located between the press heads and between the open clamp mechanisms 22, 24. The actuation of such a proximity detector would then serve to actuate the connected clamp/press solenoid valve 182.

When the clamp/press solenoid valve 182 is actuated, pilot air is directed via lines 192, 194, respectively, to a pilot-operated press control valve 196 and a pilot-operated clamp control valve 198.

The pilot fluid in line 194 causes the clamp control valve 198 to switch from a release position (FIG. 2) to a clamp position. In the release position, the lines 74 between the clamp control valve 198 and the clamp mechanisms 22, 24 are connected to a vacuum return 206, thereby moving the clamp mechanism pistons 72 to hold open the clamps 22, 24.

Preferably, the vacuum return 206 is a compact mechanism mounted to the platform 46 and comprising a master and slave cylinder assembly. The master cylinder is connected to the air source for forcing the master cylinder to drive a connected piston in the associated slave cylinder, thereby creating a partial-vacuum chamber within the slave cylinder. That chamber is placed in fluid communication with lines 74 whenever the clamp control valve 198 is in the release position.

In the clamp position, the clamp control valve 198 directs pressurized air from regulator 178 over lines 200, 202 to the clamp mechanisms 22, 24 for moving the pistons 72 to close the clamp mechanisms against the free ends 64, 66 of the test sample 30.

The closing of the clamps 22, 24 is substantially coincident with the actuation of the press cylinder 150 to force the movable press head 36 against the stationary press head 38 with the bonding region 35 of the test sample 30 pressed therebetween. In this regard, the press control valve 196 is moved in response to pilot air in line 192 to direct pressurized air entering the press control valve 196 over line 204 to the line 205 extending between the press control valve 196 and the press cylinder 150. When the pressurized air is directed by the press control valve 196 to line 205, the press cylinder 150 moves the press head 36 in a direction for pressing the bonding region 35 against the opposing press head 38.

At the time the clamp/press solenoid valve 182 is actuated, the pull solenoid valve 184 is not actuated. Accordingly, no pilot air is applied over the pilot lines 208, 210 that emanate from the pull solenoid valve 184. In the absence of pilot air over line 208, a connected pilot-operated pressure select valve 212 remains in a position (FIG. 2) for directing relatively high-pressure air from regulator 176 through line 204 and through press control valve 196 and over line 205 to the press cylinder 150. In short, the actuation of the clamp/press solenoid valve 182 directs relatively high-pressure air to the press cylinder 150 for the purpose of facilitating the adhesive bonding that occurs the bonding region 35 of the test sample 30.

Preferably, the regulator 176 is adjustable to provide any selected air pressure over line 204 so that the bonding pressure applied by the press cylinder 150 to the test sample 30 will vary accordingly. Such an adjustment may be initiated, for example, by an associated servomechanism for varying the pressure to simulate an industrial production process.

As noted earlier, the press heads 36, 38 are heated via temperature controllers 140 so that the bonding region 35 will be heated to a preselected temperature.

After the movable press head 36 has been held against the bonding region 35 for a preselected cure time, the pressure in the press cylinder 150 is reduced and the pull cylinder 40 is actuated to pull the clamp mechanism 24 away from clamp 22 while the test sample 30 remains clamped. To this end, the pull solenoid valve 184 is actuated either manually, via an associated switch 214, or by the output signal from a countdown timer 216 that is started when the clamp/press solenoid valve 182 is actuated via switch 190. The countdown timer 216 can include a display 218 for indicating the selected cure time.

When the pull solenoid valve 184 is actuated via switch 214, pilot air in line 208 actuates pilot-operated pressure select valve 212 to move that valve to a position wherein relatively low-pressure air from regulator 174 is directed over line 204 through press control valve 196 to the press cylinder 150 via line 205. The low-pressure air reaching press cylinder 150 is sufficient for holding the movable press head 36 lightly against the bonding region 35 of the test sample 30 so that the bonding region does not bend or twist while the clamp mechanism 24 is being moved by the pull cylinder 40 for testing the adhesive bond strength. Preferably, the pressure applied by the movable press head 36 during the time the pull cylinder is retracting the clamp mechanism 24 is between about 40 and 80 kilopascals for a test sample formed of strips of wood.

Preferably, the regulator 174 is adjustable to provide any selected air pressure (over lines 204 and 205) to the movable press head 36 as the clamps mechanism 24 is retracted. Consequently, the reduced pressure applied by press head 36 can be adjusted so that the bonding region of test samples of various types may be securely held straight during the test without generating excessive frictional resistance to the applied shear force.

Air pressure in pilot line 210 (resulting from actuation of the pull solenoid valve 184) switches a pull control valve 220 into a position for directing air from regulator 178 over line 221 for causing the pull cylinder 40 to pull the attached clamp mechanism 24 away from the opposing clamp mechanism 22.

A regulator 225 in the form of an adjustable flow control valve is provided in line 221. Adjustment of that regulator 225 has the effect of adjusting the "pull" rate with which the pull cylinder 40 retracts the clamp mechanism 24. As a result, the rate with which the shear load is applied to the sample 30 may be adjusted for studying the influence of the pull rate on bond strength development.

As described earlier, the force transmitted through the test sample 30 by movement of the clamp mechanism 24 away from the opposing clamp mechanism 22 is detected by the load cell 42 and displayed on the display device 44. Preferably, the device 44 displays the maximum force developed in the sample 30 immediately prior to failure, which force can be correlated to the adhesive bond strength developed in the sample 30.

It can be appreciated that all data pertaining to the bonding pressure, curing time and bonding temperature, can be readily recorded either manually or with the aid of a digital computer for establishing the relationship among these process variables and the adhesive bond strength achieved by the test sample. As noted earlier, these relationships are useful for optimizing any of a number of manufacturing processes that include an adhesive bonding step.

As noted earlier, additional switching mechanisms may be included for automating the testing process. For example, an electronic proximity detector 171 (FIG. 2) may be located near the movable clamp mechanism 24 for actuation whenever the clamp mechanism reaches its fully retracted position after the bond fails. The proximity switch 171 is connected via line 173 to the clamp/press solenoid valve 182 and to pull solenoid valve 184 for inactivating those valves so that the associated press control valve 196 and pull control valve 220 direct air over lines 207 and 223, respectively, to open the clamps 22, 24 and press cylinder 150, and to advance the clamp mechanism 24 to its original position near the other clamp mechanism 22. The device is now ready to receive another sample and the test process is repeated.

Although the invention has been shown and described in the context of a preferred embodiment, it will be apparent to those skilled in the art that changes and modifications may be made thereto without departing from the invention in its broader aspects. Accordingly, the appended claims are intended to cover all such changes and modifications as follow the spirit and scope of the invention.

I claim:

1. A device for testing an adhesive bond between overlapping portions of first and second parts, comprising:
   a first clamp operable for clamping a first part;
   a second clamp operable for clamping a second part with a portion of the first part overlapping and adhesively bonded to a portion of the second part;
   a pair of press members, one press member being movable for pressing together the overlapping portions of the first and second parts;
   heat means connected to at least one of the press members, the heat means controllable for applying heat to the overlapping portions of the first and second parts while the overlapping portions are pressed together;
   a temperature controller connected to the heat means and operable by the user of the device for heating the first and second portions of the overlapping portions to any selected temperature of a range of temperatures; and
   shearing means actuatable after a preselected time for forcing the first clamp and the second clamp apart to force the first part away from the second part.

2. The device according to claim 1 wherein the temperature controller includes a heater embedded within the movable press member and a thermocouple embedded within the movable press member.

3. The device according to claim 1 further comprising pressure means connected to the movable press member for adjusting the amount of pressure applied by the movable press member in pressing together the overlapping portions of the first and second parts.

4. The device according to claim 3 further comprising control means for controlling movement of the movable press member and for actuating the shearing means, the control means including timing means for establishing the time interval that the overlapping portions are pressed together before the shearing means is actuated.

5. The device according to claim 4 further comprising measuring means for measuring the force applied by the shearing means in forcing the first part away from the second part.

6. The device according to claim 3 wherein the pressure means reduces without eliminating the pressure applied by the movable press member as the shearing means forces the first part away from the second part.

7. A method for testing a bonded test sample, comprising the steps of:
   securing a first part of the sample;
   securing a second part of the sample so that a portion of the first part overlaps and adheres to a portion of the second part;
   applying a preselected pressure by two press heads to respective overlapped portions;
   applying a preselected amount of heat to the two press heads and to the overlapping portions using a heater connected to at least one of the press heads;
   reducing, without eliminating, the pressure applied to the overlapped portions before shearing apart the overlapping portions after a predetermined time interval;
   shearing apart the overlapping portions; and
   measuring and displaying a force required to shear apart the overlapping portions, and a controlling and displaying a time the preselected pressure is applied to the overlapping portions.

8. A device for testing an adhesive bond between overlapping portions of first and second parts, comprising:
   a first clamp operable for clamping a first part;
   a second clamp operable for clamping a second part with a portion of the first part overlapping and adhesively bonded to a portion of the second part;
   a first press member;
   a second press member movable in a first direction for pressing the overlapping portions of the first and second parts against the first press member to apply a bonding pressure to the overlapping portions;
   heat means connected to at least one of the press members for heating the press member;
   an actuator for moving the first clamp in a second direction away from the second clamp to pull the overlapping portions apart after a predetermined time interval; and
   control means connected to the press members for reducing the bonding pressure as the actuator begins to move the first clamp away from the second clamp.

9. The device according to claim 8 wherein the control means includes temperature control means for varying the temperature of the first and second press members.

10. The device according to claim 9 wherein the temperature control means include a temperature controller connected to both press members and operable by the user of the device for heating the press members to any selected temperature of a range of temperatures.

11. The device according to claim 10 wherein the temperature control means includes a heater embedded in each press head and a thermocouple embedded within each press member.

12. The device according to claim 8 wherein the first direction is substantially perpendicular to the second direction.

13. The device according to claim 12 further comprising measuring means for measuring the force necessary to force the overlapping portions apart.

14. The device according to claim 8 wherein the control means keeps the press members in contact with the overlapping portions while the actuator moves the first clamp away from the second clamp.

15. The device according to claim 8 wherein the first clamp includes first and second clamp plates between which the first part is clamped, the first clamp plate being mounted for pivotal movement in response to pressure applied to the first clamp plate.

16. The device according to claim 15 wherein the position of the first clamp plate is adjustable relative to the second clamp plate.

17. The device according to claim 8 wherein the control means includes timing means for establishing the time interval that the overlapping portions are pressed together before the actuator begins to move the first clamp away from the second clamp.

* * * * *